US009254200B2

(12) United States Patent
Galea et al.

(10) Patent No.: US 9,254,200 B2
(45) Date of Patent: Feb. 9, 2016

(54) ACTIVE PROSTHETIC SOCKET

(75) Inventors: Anna M. Galea, Stow, MA (US); Kristen LeRoy, Somerville, MA (US); Thieu Q. Truong, North Easton, MA (US)

(73) Assignee: Vivonics, Inc., Waltham, MA (US)

( * ) Notice: Subject to any disclaimer, the term of this patent is extended or adjusted under 35 U.S.C. 154(b) by 0 days.

(21) Appl. No.: 13/506,473

(22) Filed: Apr. 20, 2012

(65) Prior Publication Data
US 2012/0271433 A1  Oct. 25, 2012

Related U.S. Application Data

(60) Provisional application No. 61/517,498, filed on Apr. 20, 2011.

(51) Int. Cl.
*A61F 2/80* (2006.01)
*A61F 2/78* (2006.01)
*A61F 5/01* (2006.01)

(52) U.S. Cl.
CPC .............. *A61F 2/7812* (2013.01); *A61F 2/80* (2013.01); *A61F 5/01* (2013.01); *Y10T 442/2008* (2015.04)

(58) Field of Classification Search
CPC ....... A61F 2/78; A61F 2/7812; A61F 2/7843; A61F 2002/741; A61F 2002/745; A61F 2002/747; A61F 2002/748; A61F 2002/5012; A61F 2002/5032; A61F 2/80; A61F 2002/802
USPC ...................................................... 623/32–38
See application file for complete search history.

(56) References Cited

U.S. PATENT DOCUMENTS

| 5,314,497 A * | 5/1994 | Fay et al. .................... 623/34 |
| 6,585,774 B2 | 7/2003 | Dean, Jr. et al. |
| 7,655,049 B2 * | 2/2010 | Phillips ....................... 623/37 |
| 7,947,085 B2 * | 5/2011 | Haines et al. ................ 623/24 |
| 2009/0271000 A1 * | 10/2009 | Altobelli et al. ............. 623/37 |

* cited by examiner

*Primary Examiner* — Bruce E Snow
(74) *Attorney, Agent, or Firm* — Iandiorio Teska & Coleman, LLP

(57) ABSTRACT

An active prosthetic socket including a prosthetic socket shaped to fit a residual limb. An active adjustment system is integrated with the prosthetic socket and is configured to dynamically adjust the fit of the active prosthetic socket to the residual limb of a user during ambulation or motion.

2 Claims, 8 Drawing Sheets

ACTIVE PROSTHETIC SOCKET

RELATED APPLICATIONS

This application claims benefit of and priority to U.S. Provisional Application Ser. No. 61/517,498 filed Apr. 20, 2011, under 35 U.S.C. §§119, 120, 363, 365, and 37 C.F.R. §1.55 and §1.78, incorporated herein by this reference.

GOVERNMENT RIGHTS

This invention was made with U.S. Government support under Contract No. W81XWH-07-C-0094 by the Army. The Government may have certain rights in certain aspects of the subject invention.

FIELD OF THE INVENTION

This invention relates to an active prosthetic socket.

BACKGROUND OF THE INVENTION

One conventional prosthetic socket device which attempts to address residual limb volume changes during ambulation or motion is a vacuum-assisted socket system (VASS). The VASS uses a vacuum to regulate residual limb volume fluctuation and decrease perspiration. However, the VASS may not be effective, is bulky and heavy.

Another conventional prosthetic socket is an air pressurized active prosthetic socket device which attempts to minimize residual limb volume by allowing the user to adjust the air level of the device to the comfort level of the user. However, the air pressurized active prosthetic socket may be ineffective because it is rotationally unstable.

Although the conventional systems discussed above attempt to maintain adequate socket-limb contact during use of the prosthetic socket, they do not account for the shape changes that occur within the residual limb during ambulation or motion. Thus, there is a need for a truly active prosthetic socket which provides for changes in the socket attendant to changes in the limb during completion of motion.

SUMMARY OF THE INVENTION

In one aspect, an active prosthetic socket is featured including a prosthetic socket shaped to fit a residual limb. An active adjustment system is integrated with the prosthetic socket and is configured to dynamically adjust the fit of the prosthetic socket to the residual limb of a user during ambulation or motion.

In one embodiment, the active adjustment subsystem may include one or more active device configured to change size or shape during ambulation to dynamically adjust the fit of the active prosthetic socket to the residual limb during ambulation. The one or more active devices may be disposed at predetermined locations in or on the prosthetic socket.

The one or more active devices may include at least one actuator bladder and at least one active bladder. The at least one actuator bladder and the at least one active bladder may be filled with a gas. The at least one actuator bladder and the at least one active bladder may be filled with a liquid. The at least one actuator bladder and the at least one active bladder may be coupled to each other by tubing. The active prosthetic socket may include one or more valves coupled to the tubing and between the at least one actuator bladder and the at least one active bladder configured to control the flow of a liquid or gas between the at least one actuator bladder and the at least one active bladder to dynamically adjust the fit of the active prosthetic socket to the residual limb during ambulation. The active adjustment subsystem may include one or more active bladders disposed at predetermined locations in or on the prosthetic socket. The active prosthetic socket may include at least one sensor configured to determine when the active bladders are in contact with the residual limb during ambulation. The active prosthetic socket may include a reservoir of a pressurized gas or liquid. The at least one sensor may include a pressure sensor disposed on or near the one or more active bladders. The at least one sensor may include an electromyography sensor disposed at predetermined locations in the prosthetic socket. The at least one sensor may include an electromyography sensor disposed on or near the one or more active bladders. The at least one sensor may include an accelerometer coupled to the prosthetic socket configured to determine the gait cycle of a user. The active adjustment subsystem may be configured to fill the active bladders with the gas or liquid when the sensor senses the active bladders are not in contact with the residual limb to dynamically adjust the fit of the active prosthetic socket to the residual limb during ambulation. The active prosthetic socket may include a control subsystem coupled to the active bladders, the sensor, and the accelerometer configured to dynamically adjust the fit of the active prosthetic socket to the residual limb of the user during ambulation or motion. The active adjustment subsystem may include at last one electro-active polymer component disposed at predetermined locations in or on the prosthetic socket. The active prosthetic socket may include at least one sensor configured to sense if the shape of the residual limb is changing. The at least one sensor may include an electromyography sensor disposed at predetermined locations on the prosthetic socket. The at least one sensor may include a pressure sensor disposed on or near the electro-active polymer component. The active prosthetic socket may include an accelerometer coupled to the prosthetic socket configured to determine the gait cycle of a user. The active adjustment subsystem may be configured to expand the electro-active polymers when the at least one electromyography sensor determines the electro-active polymers are not in contact with the residual limb to dynamically adjust the fit of the active prosthetic socket to the residual limb during ambulation. The active prosthetic socket may include a control subsystem coupled to the electro-active polymers, the electromyography sensor, and the accelerometer configured to dynamically adjust the fit of the active prosthetic socket to the residual limb of the user during ambulation or motion. The active prosthetic socket may include a frame. The active adjustment system may be located on or in the frame.

The subject invention, however, in other embodiments, need not achieve all these objectives and the claims hereof should not be limited to structures or methods capable of achieving these objectives.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
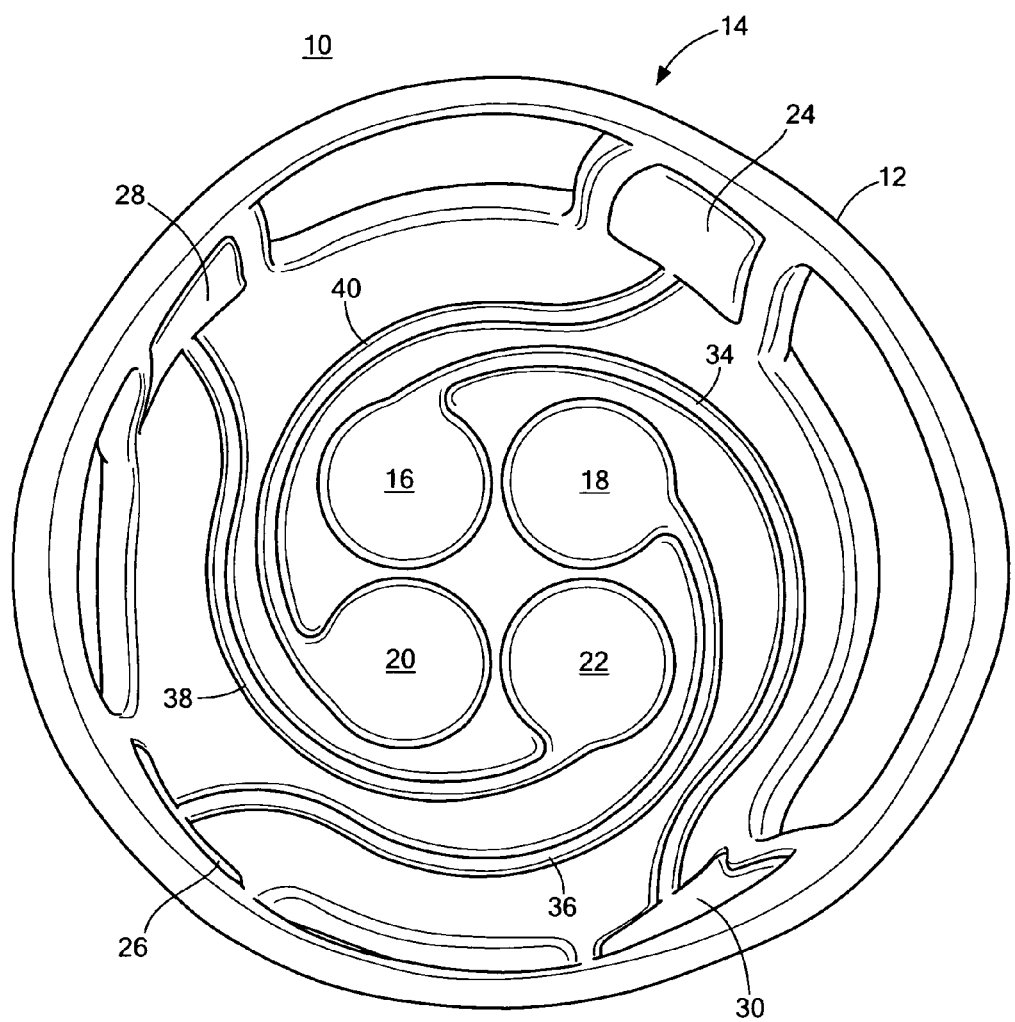
FIG. 1 is a three-dimensional top-view of one embodiment of the active prosthetic socket of this invention.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

There is shown in FIG. 1 one embodiment of active prosthetic socket 10 of this invention. Active prosthetic socket 10 includes prosthetic socket 12 shaped to fit a residual limb of an amputee. Active prosthetic socket 10 also includes active adjustment system 14 integrated with prosthetic socket 12 which dynamically adjusts the fit of prosthetic socket 12 to the residual limb of a user during ambulation or motion, e.g., walking, running, sitting, standing, and the like.

Active adjustment system 14 preferably includes one or more active devices disposed at predetermined locations in/on prosthetic socket 12. The active devices are designed to change size or shape during ambulation or motion to dynamically adjust the fit of the active prosthetic socket 10 to the residual limb. In one example, the active devices include actuator bladders 16, 18, 20, and 22 coupled to active bladders 24, 26, 28, and 30 via tubing or lines 34, 36, 38, and 40, respectively. Preferably, actuator bladders 16-22 are located proximate the bottom of prosthetic socket 12 and active bladders 24-30 are located proximate the top of prosthetic socket 12 as shown. Actuator bladders 16-22 and active bladders 24-30 are preferably filled with a gas or liquid.

In one exemplary operation, one or more of actuator bladders 16-22 and one or more of active bladders 24-30 change size in response to a user's ambulation or motion to dynamically adjust the fit of active prosthetic socket 10 to the residual limb. For example, actuator bladders 16-22 are compressed as a prosthetic leg and foot attached to active prosthetic socket 10 strikes the ground. This causes the fluid or gas in actuator bladders 16-22 to be transferred via tubing 36-40 to active bladders 24-30. Active bladders 24-30 then compress on the residual limb and increase pressure near the top of prosthetic socket 12 to provide a snug fit of active prosthetic socket 10 to the residual limb. When the prosthetic leg and foot attached to prosthetic socket 12 moves upward from the ground, the fluid from active bladders 24-30 is then transferred back to actuator bladders 16-22. The result is active prosthetic socket 10 dynamically, in real-time, adjusts the fit of prosthetic socket 12 to the residual limb during ambulation or motion.

Figure 2:
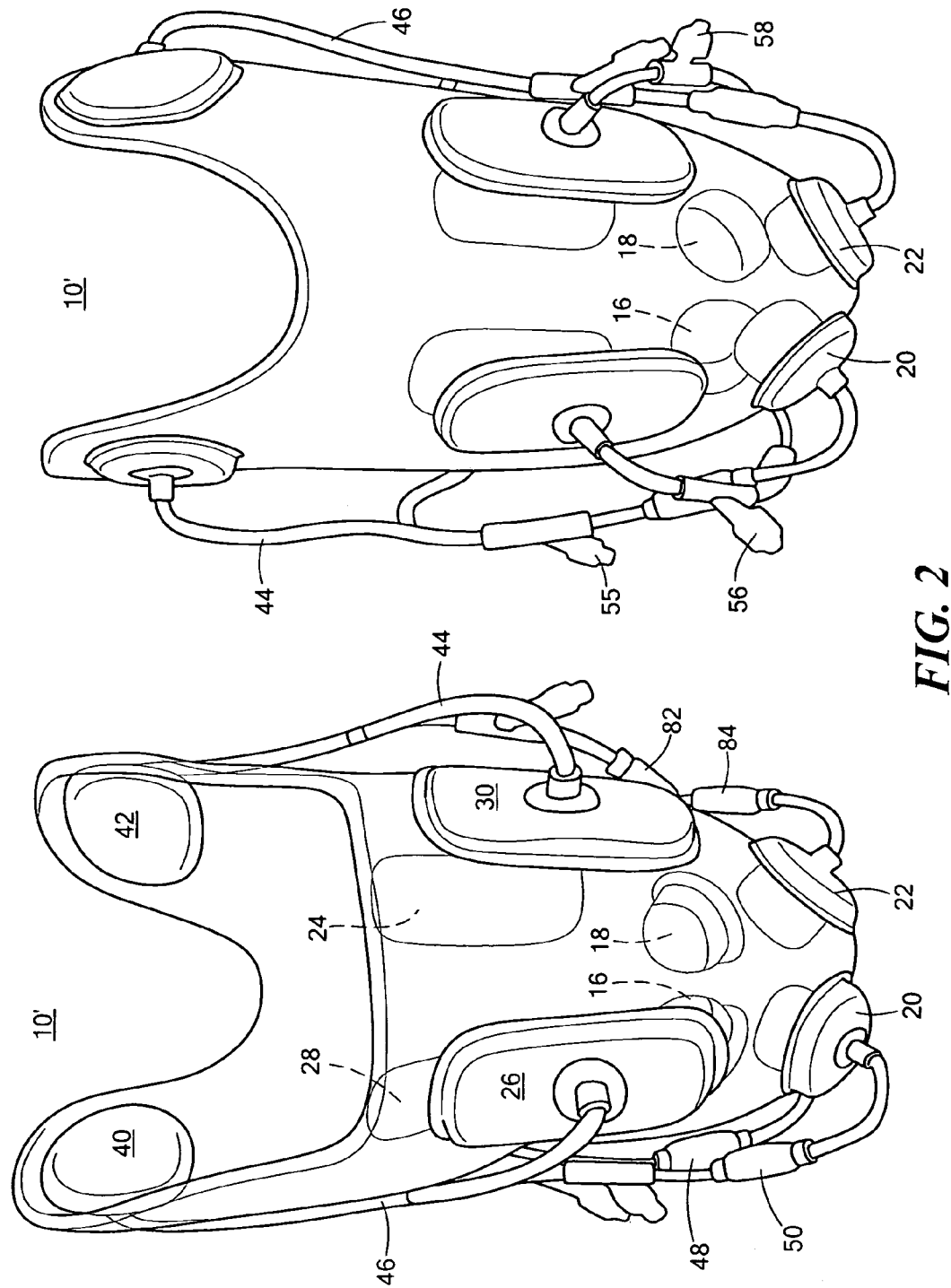
FIG. 2 depicts three-dimensional views of another embodiment of the active prosthetic socket of this invention.
Figure 3:
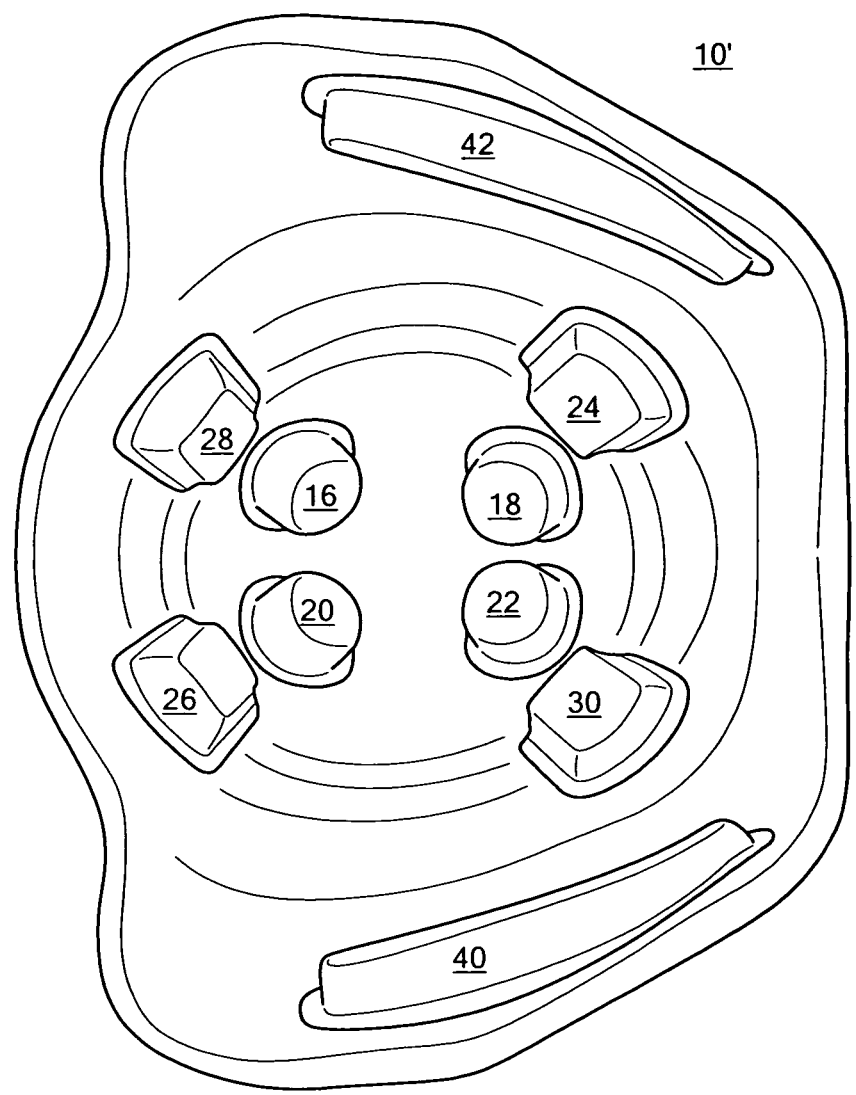
FIG. 3 is a three-dimensional top-view of the active prosthetic socket shown in FIG. 2.

Active prosthetic socket 10', FIG. 2, where like parts have like numbers, similarly includes actuator bladders 16-22 and active bladders 24-30 as discussed above with reference to FIG. 1. In this example, active prosthetic socket 10' also includes active bladders 40 and 42 coupled to actuator bladders 16-22 by tubing or lines 44 and 46 as shown. Active prosthetic socket 10 also preferably includes valves, e.g., valves 48, 50, 52, and 54 which regulate the flow of the liquid or gas in actuator bladders 24-30 to or from active bladders 24-30. Ports 55, 56, and 58 may be used to fill actuator bladders 16-22 and active bladders 24-30 with a gas or fluid. FIG. 3 shows a top-view of actuator bladders 16-22 and active bladders 24-30 and 40-42.

Figure 4:
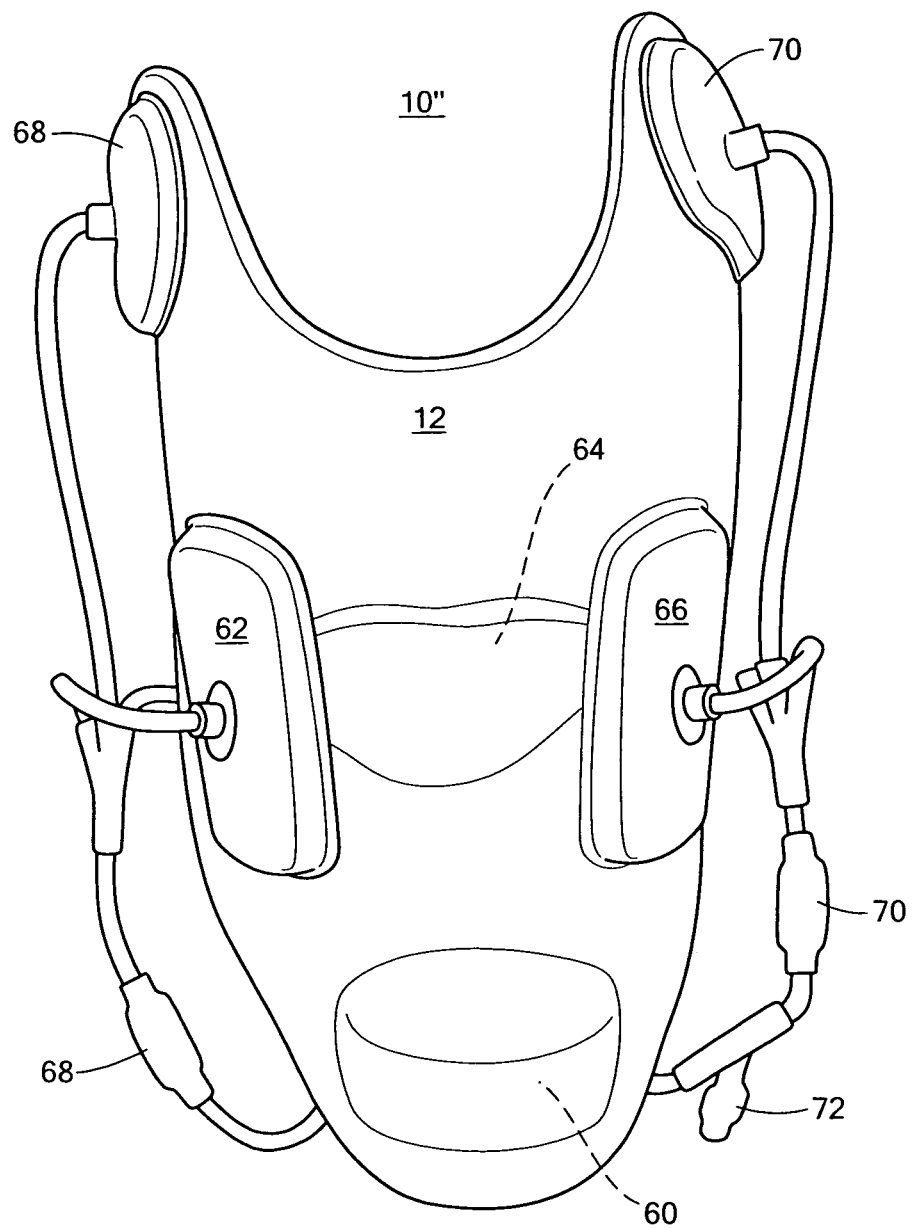
FIG. 4 is a three-dimensional view of another embodiment of the active prosthetic socket of this invention.
Figure 5:
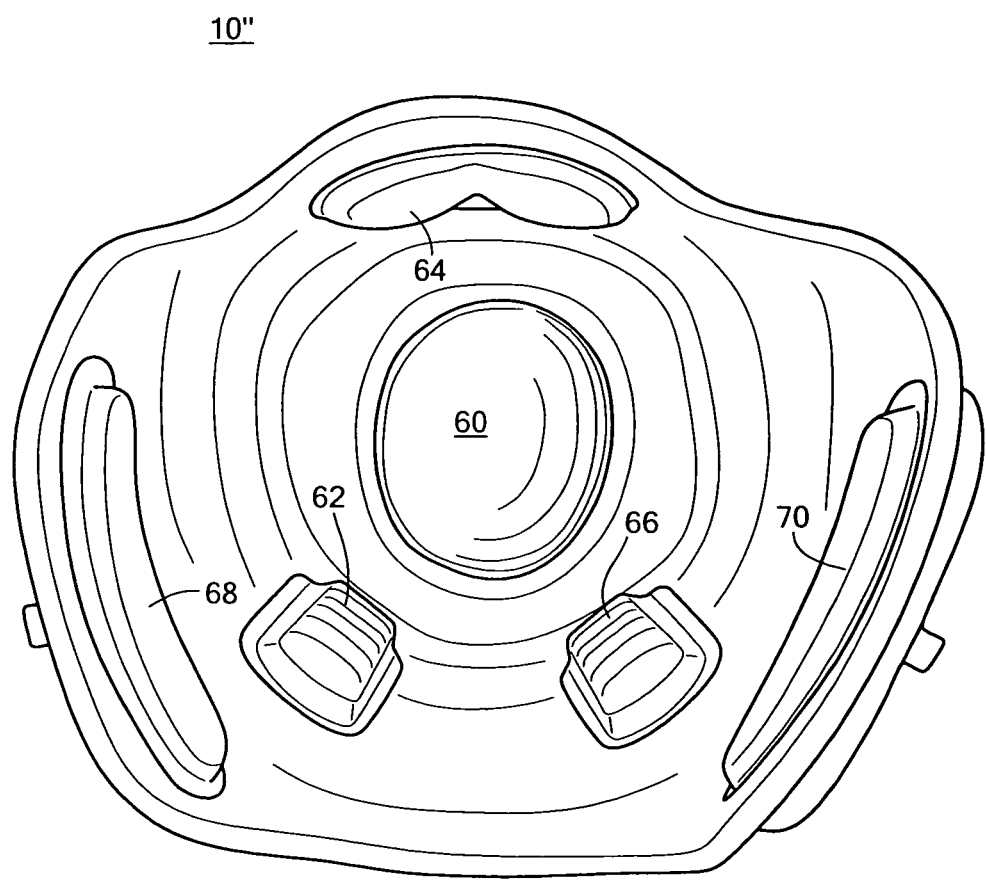
FIG. 5 is a three-dimensional top-view of the active prosthetic socket shown in FIG. 4.

Although as discussed above with reference to FIGS. 1-3, active prosthetic socket 10, 10' is shown having four actuator bladders 16-22 located at the bottom of prosthetic device 12, this is not a necessary limitation of this invention. In other designs, active prosthetic socket 10", FIG. 4, may include only one actuator bladder 60 preferably located at the bottom of prosthetic socket 12. In this example, actuator bladder 60 is connected to at least one active bladder, e.g., five active bladders 62, 64, 66, 68, and 70 at the various locations shown on prosthetic socket 12 via the tubing or lines as shown. Active prosthetic socket 10" also may include valves 68 and 70 which regulate the flow of the fluid or gas to and from actuator bladder 60 and active bladders 62-70, similar as discussed above with reference to FIGS. 1-3. Port 72, FIG. 4, may be used to fill actuator bladder 60 and active bladders 62-70 with a gas or fluid. FIG. 5, where like parts have like numbers, shows a top view of active prosthetic socket 10".

Figure 6:
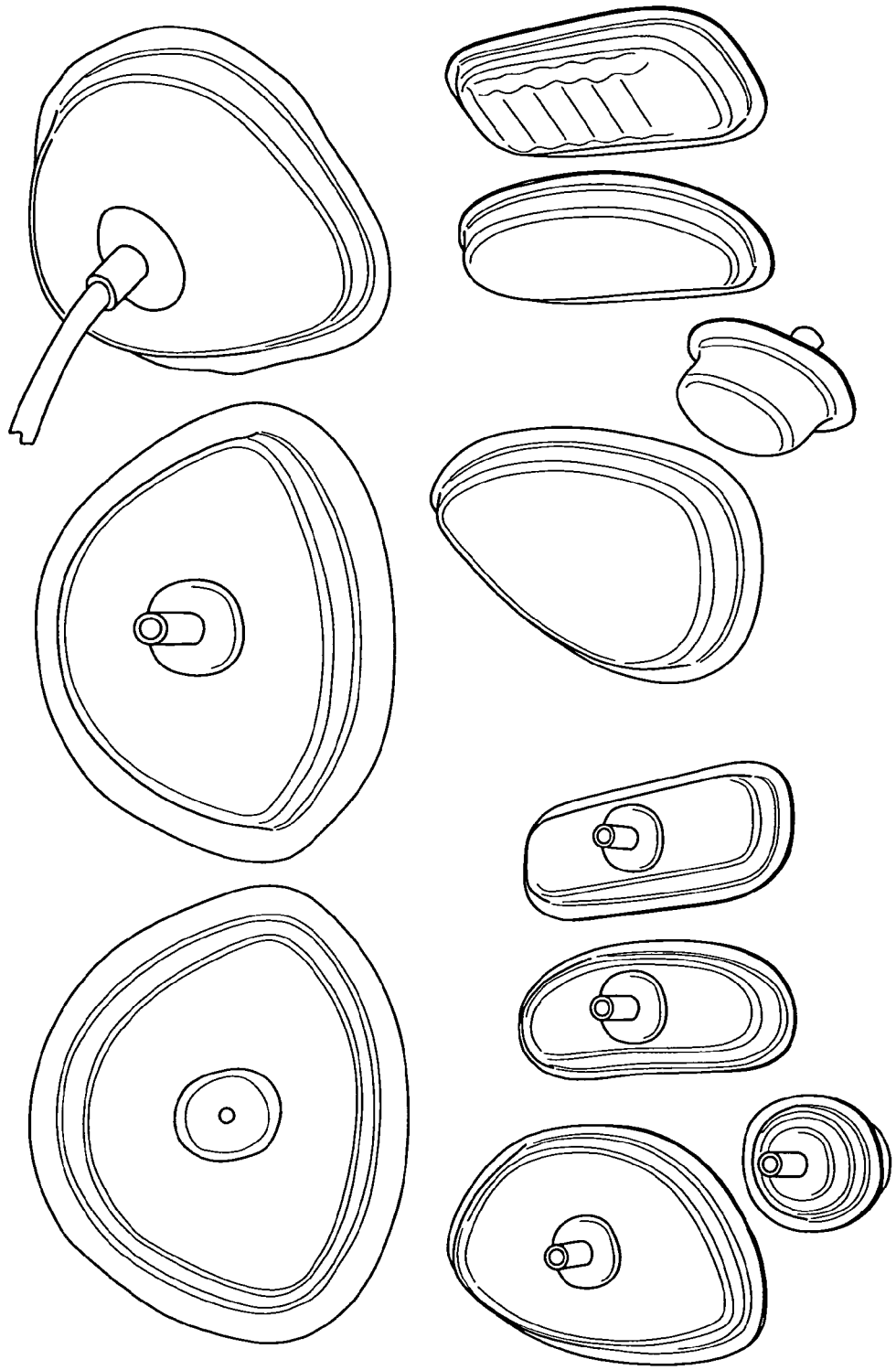
FIG. 6 shows three-dimensional views of various shapes which may be used for the actuator bladder(s) and active bladders shown in one or more of FIGS. 1-5.

The actuator bladders and active bladders discussed above with reference to FIGS. 1-5 may have the shapes as shown or may have various other shapes as, e.g., shown in FIG. 6.

Figure 7:
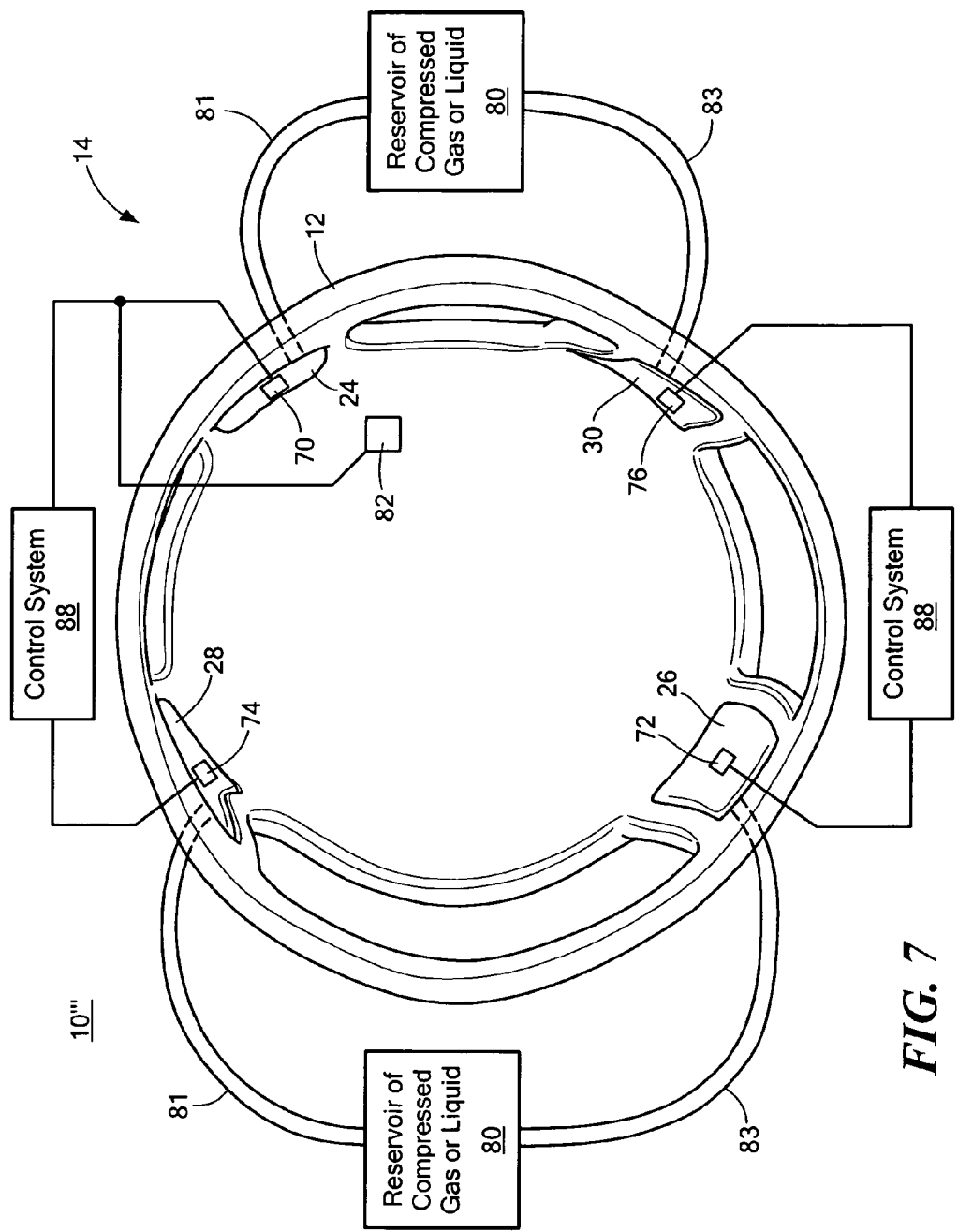
FIG. 7 is a three-dimensional top-view of another embodiment of the active prosthetic socket of this invention.

Active prosthetic socket 10''', FIG. 7, where like parts have like numbers, includes active adjustment system 14' integrated with prosthetic socket 12 which dynamically adjusts the fit of prosthetic socket 12 to the residual limb of a user in during ambulation or motion. In this example, active adjustment system 14' includes active bladders 24-30 having a similar structure and design as discussed above with reference to FIGS. 1-5. However, in this example, active adjustment system 14', FIG. 7, does not include actuator bladders 16-22, FIGS. 1-5. Instead, in one embodiment, active adjustment system 14' includes a pressure sensor attached to each of active bladders 24-30, e.g., pressure sensor 70 attached to active bladder 24, pressure sensor 72 attached to active bladder 26, pressure sensor 74 attached to active bladder 28 and pressure sensor 76 attached to active bladder 30. Pressure sensors 70-76 sense if the active bladders 24-30 are in contact with the residual limb during ambulation or motion. When one or more of or all active bladders 24-30 are not in contact with the residual limb, active adjustment system 14' fills one or more or all of active bladders 24-30 with a gas or liquid from reservoir 80 of pressurized gas or liquid 80 via tubing or lines 81 and 83 to dynamically adjust the fit of active prosthetic socket 10" to the residual limb. Reservoir 80 may be located on a prosthetic leg, proximate to active prosthetic socket 10''', or in similar locations. A pump (not shown) for the gas or liquid may also be disposed on the prosthetic leg or proximate prosthetic socket 10'''. In one design, active adjustment system 14' may include an accelerometer, e.g., accelerometer 82, coupled to prosthetic socket 12 which determines the gait cycle of a user. In one embodiment, active prosthetic socket 10''' preferably includes control subsystem 88 coupled to sensors 70-76 and accelerometer 82 which controls active bladders 24-30 and reservoir 80 to dynamically adjust the fit of the prosthetic socket to the residual limb of the user during ambulation or motion.

Figure 8:
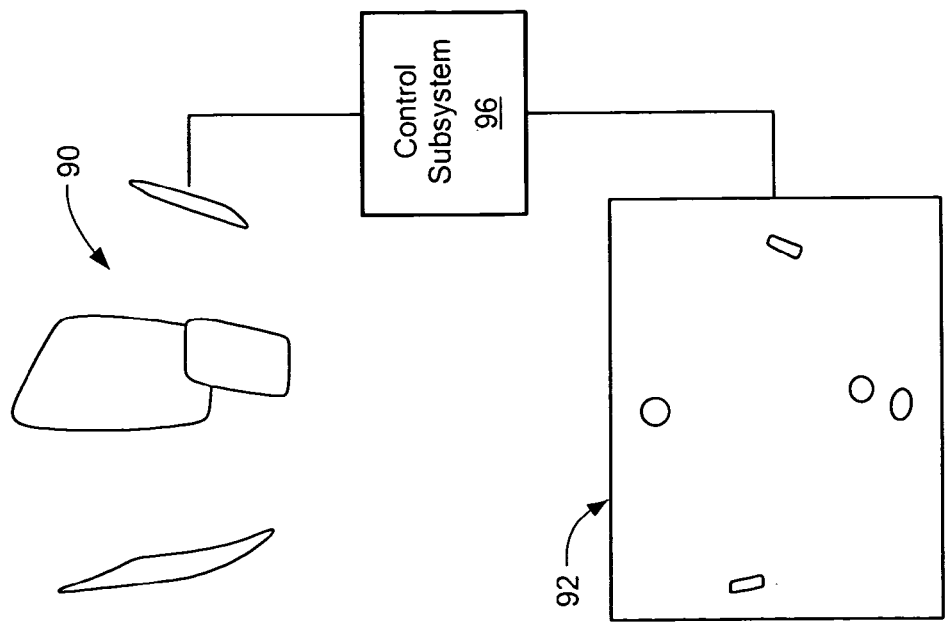
FIG. 8 shows three-dimensional views of electro-active polymers and electromyography sensors which may used in place of the actuator bladders and pressure sensors, respectively, shown in FIG. 7, in accordance with another embodiment of this invention.

Although as discussed above with reference to FIG. 7, active adjustment system 14' may include a pressure sensor attached to each of active bladders 24-30 and reservoir 80 which fills active bladders 24-30 when the residual limb is not in contact with prosthetic socket 12 during ambulation or motion, this is not a necessary limitation of this invention. In other designs, active adjustment system 14' may include at least one electro-active polymer (EAPs), e.g., EAPs 90, FIG. 8, instead of active bladders 24-30, FIG. 7. EAPs 90, FIG. 8, are disposed at various predetermined locations in or on prosthetic socket 12, FIG. 7, similar to the locations for active bladders 24-30. In this design, active adjustment system 14' preferably includes one or more (EMGs), e.g., (EMGs) 92, FIG. 8, at desired locations in prosthetic socket 12, corresponding to selected muscles in the residual limb. The EMGs may also be used in place of pressure sensors 70-76. The EMGs 92 sense if EAPs or active bladders 24-30 are in contact with the residual limb during ambulation or motion. When the EAPs or active bladders are not in contact with the residual limb, active adjustment system 14' causes the EAPs or the active bladders to expand to dynamically adjust the fit of the prosthetic socket 12 to the residual limb during ambulation or motion. In this embodiment, active adjustment system 14' preferably includes a control subsystem 96, FIG. 8, may be coupled to electro-active polymers 90, EMGs 92, and accelerometer 82, FIG. 7, to dynamically adjust the fit of the prosthetic socket to the residual limb of the user during ambulation or motion.

Figure 9:
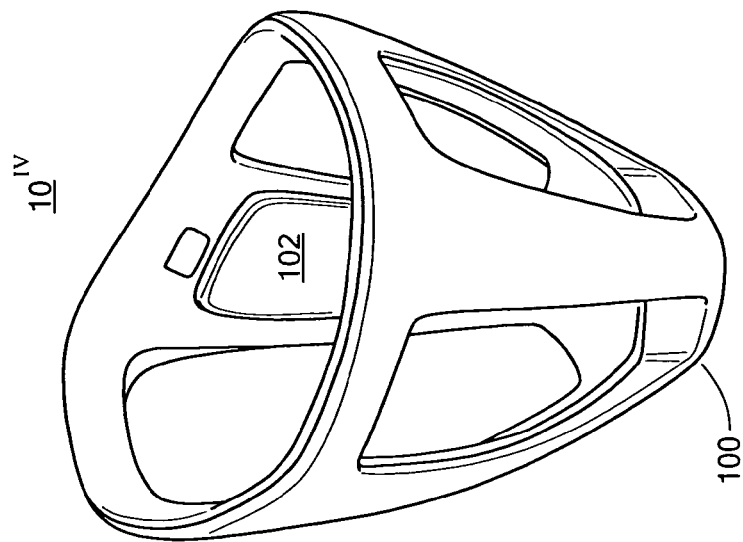
FIG. 9 shows a three-dimension view of another embodiment of the active prosthetic socket of this invention.

In another example, active prosthetic socket 10$^{IV}$, FIG. 9, preferably includes frame 100 that may house the actuator bladders, active bladders, pressure sensors, EAPs, the EMGs, and the like, discussed above. In this example, one active bladder, 102 is shown disposed in frame 100.

Although, as discussed above with reference to FIGS. 1-9, the active prosthetic socket 10 is shown for the residual limb of leg, this is not a necessary limitation of this invention, as active prosthetic socket 10 may be used for the residual limb of any part of an amputee.

Although specific features of the invention are shown in some drawings and not in others, this is for convenience only as each feature may be combined with any or all of the other features in accordance with the invention. The words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant cannot be expected to describe certain insubstantial substitutes for any claim element amended.

Other embodiments will occur to those skilled in the art and are within the following claims.

The invention claimed is:

1. An active prosthetic socket comprising:
a prosthetic socket shaped to fit a residual limb; and
an active adjustment system integrated with the prosthetic socket including:
four actuator bladders located at a rounded bottom end of the prosthetic socket;
at least two active bladders located at a middle of the prosthetic socket and at least two active bladders located at the top of the prosthetic socket, each of the active bladders fluidically coupled only to one of the four actuator bladders; and
the four actuator bladders configured to be compressed as a prosthetic leg and foot attached to the prosthetic socket strikes the ground causing fluid in the four actuator bladders to be transferred to the two active bladders at the middle of the prosthetic socket and the two active bladders at the top of the prosthetic socket such that the active bladders compress on a residual limb to provide a snug fit of the prosthetic device.

2. An active prosthetic socket comprising:
a prosthetic socket shaped to fit a residual limb; and
an active adjustment system integrated with the prosthetic socket including:
one actuator bladder located at a bottom end of the prosthetic socket;
at least two active bladders located at a middle of the prosthetic socket and at least two active bladders located at a top of the prosthetic socket, each of the active bladders fluidically coupled only to the one actuator bladder; and
the one actuator bladder configured to be compressed as a prosthetic leg and foot attached to the prosthetic socket strikes the ground causing fluid in the one actuator bladder to be transferred to the two active bladders located at the middle of the prosthetic socket and the two active bladders at the top of the prosthetic socket such that the active bladders compress on a residual limb to provide a snug fit of the prosthetic device.

* * * * *